（12） United States Patent
Tai et al.

(10) Patent No.: US 12,409,154 B2
(45) Date of Patent: Sep. 9, 2025

(54) PHARMACEUTICAL COMPOSITIONS FOR USE IN TREATING PAIN

(71) Applicants: TAIWAN LIPOSOME COMPANY, LTD., Taipei (TW); TLC BIOPHARMACEUTICALS, INC., South San Francisco, CA (US)

(72) Inventors: Tien-Tzu Tai, Taipei (TW); Yun-Long Tseng, Taipei (TW); Sheue-Fang Shih, Taipei (TW); Min-Wen Kuo, Taipei (TW); Carl Oscar Brown, Taipei (TW); Hui-Ting Wang, Taipei (TW); Weenee Yeun Ng Jao, Taipei (TW); Pei-Hsien Hu, Tapei (TW); Wan-Ni Yu, Taipei (TW); Keelung Hong, Taipei (TW); Hao-Wen Kao, South San Francisco, CA (US); Yi-Yu Lin, South San Francisco, CA (US)

(73) Assignees: TAIWAN LIPOSOME COMPANY, LTD., Taipei (TW); TLC BIOPHARMACEUTICALS, INC., South San Francisco, CA (US)

( * ) Notice: Subject to any disclaimer, the term of this patent is extended or adjusted under 35 U.S.C. 154(b) by 1051 days.

(21) Appl. No.: 17/433,719

(22) PCT Filed: Feb. 26, 2020

(86) PCT No.: PCT/US2020/019806
§ 371 (c)(1),
(2) Date: Aug. 25, 2021

(87) PCT Pub. No.: WO2020/176568
PCT Pub. Date: Sep. 3, 2020

(65) Prior Publication Data
US 2022/0071934 A1 Mar. 10, 2022

Related U.S. Application Data

(60) Provisional application No. 62/848,286, filed on May 15, 2019, provisional application No. 62/810,378, filed on Feb. 26, 2019.

(51) Int. Cl.
*A61K 31/167* (2006.01)
*A61K 9/127* (2025.01)
*A61K 47/24* (2006.01)
*A61P 23/02* (2006.01)

(52) U.S. Cl.
CPC ............ *A61K 31/167* (2013.01); *A61K 9/127* (2013.01); *A61K 47/24* (2013.01); *A61P 23/02* (2018.01)

(58) Field of Classification Search
CPC .... A61K 9/127; A61K 31/445; A61K 9/0019; A61K 31/167; A61K 9/1277; A61K 31/485; A61K 9/1271; A61K 2300/00; A61K 45/06; A61K 47/02; A61K 47/12; A61K 9/0085; A61K 47/24; A61K 31/40; A61K 9/0002; A61K 31/192; A61K 31/407; A61K 31/4458; A61K 31/661; A61K 47/14; A61K 9/107; A61K 47/22; A61K 47/26; A61K 9/1278; A61K 31/4375; A61K 31/451; A61K 31/66; A61K 47/28; A61K 9/06; A61K 9/1075; A61K 9/1272; A61K 9/113; A61K 9/1273; A61P 23/02; A61P 23/00; A61P 25/02
See application file for complete search history.

(56) References Cited

U.S. PATENT DOCUMENTS

2004/0018230 A1  1/2004  Grant et al.
2015/0250724 A1* 9/2015  Yamashita ........... A61K 9/0019
                                                                    604/272
2020/0188374 A1  6/2020  Hong et al.

FOREIGN PATENT DOCUMENTS

| CN | 108379269 A | 8/2018 |
| CN | 111182889 A | 5/2020 |
| WO | 99/49849 | 10/1999 |
| WO | 2013/146386 A1 | 10/2013 |
| WO | 2014/046191 A1 | 3/2014 |
| WO | 2019/191731 A1 | 10/2019 |

OTHER PUBLICATIONS

History of Changes for Study: NCT03591146, Phase I/II Dose-escalation Study to Evaluate Safety, PK and Efficacy of TLC590 for Postsurgical Pain Management, Clinical Trials. gov archive [online], Aug. 20, 2018. [6 pages].
EXPAREL Prescribing Information, Revised Apr. 2018.
A basic guide to particle characterization, Malvern Instruments Worldwide, 2012, pp. 1-26.
International Search Report and Written Opinion of corresponding PCT application PCT/US2020/019806, mailed on May 28, 2020.
Pettersson et al. "High-Dose Ropivacaine Wound Infiltration for Pain Relief After Inguinal Hernia Repair, A Clinical and Pharmacokinetic Evaluation", Regional Anesthesia and Pain Medicine 23(2): 189-196, 1998 [8 pages].

* cited by examiner

*Primary Examiner* — Audrea B Coniglio
(74) *Attorney, Agent, or Firm* — LEASON ELLIS LLP (57) ABSTRACT

Provided is a pharmaceutical composition for use in treating postsurgical pain. The pharmaceutical composition comprises a lipid-based complex. The lipid-based complex comprises an amide-type anesthetic and at least one lipid, wherein a molar ratio of the amide-type anesthetic to the at least one lipid of the lipid-based complex is at least 0.5:1. The total amount of the amide-type anesthetic is at least 1.5 to 5 times of a standard therapeutic dose for treating postsurgical pain with the amide-type anesthetic to achieve an improved pain control with desired prolonged analgesic effect.

18 Claims, 5 Drawing Sheets

PHARMACEUTICAL COMPOSITIONS FOR USE IN TREATING PAIN

BACKGROUND

Technical Field

The present disclosure relates to a use of an anesthetic composition in pain control. The present disclosure relates to a method of controlling pain.

Description of Related Art

Local anesthetics have been widely used for surgical anesthesia and postsurgical analgesia, due to their ability to reversibly inhibit the voltage-gated sodium channels and block action potentials in nerve fibers. Yet at high plasma levels this type of anesthetic also interacts with other ion channels to induce acute neural and cardiac toxicity, as well as allergic reactions. So-called local anesthetic systemic toxicity (LAST) is always a potential complication of all local anesthetics, and any route of administration, and may be fatal.

Ropivacaine was introduced in 1996 as a pure S(−) isomer amide-type local anesthetic and approved by the Food and Drug Administration (FDA) in 2000 under the trade name Naropin®. It exhibits considerably less lipophilicity and motor block, and has a greater safety margin due to reduced cardiotoxicity, compared to bupivacaine (Marcaine®). Naropin® can be administered via different injection routes, including spinal anesthesia, epidural anesthesia, regional block, and local infiltration. Despite having many advantages over other local anesthetics, the duration of analgesia after single-administration of 0.5% Naropin® (200 mg ropivacaine hydrochloride injection) via wound infiltration was only about 6 to 8 hours. It is insufficient to cover a significant amount of recovery time after surgery and specifically the critical 3-day post-operative window.

Local anesthetics have the limitation of short duration of action, and the risk of LAST. NSAIDs and infiltration with local anesthetic agents (e.g., ropivacaine hydrochloride) are also widely accepted as a postsurgical pain management regimen. However, there are some potential safety concerns regarding the use of NSAIDs, and the duration of postsurgical analgesia with local anesthetic agents is generally limited to about 8 hours. The medical objective is to relieve acute postsurgical pain without use of opioids for the critical 2-4 day window after surgery. Thus, there is an unmet medical need to provide a long duration, non-opioid, safer, and more effective method of managing post-operative pain with a single-dose perioperative administration of a drug product.

When utilizing prolonged blocks by local anesthetics, either through continuous infusion or through repeated bolus administration, there is a high risk of reaching a toxic plasma concentration or inducing local neural injury. Evidences supporting the neurotoxicity of local anesthetics emerged from the analysis of paraesthesia persistency after local anesthetic drug injection. The severity of paraesthesia is related to the length of the altered sensations; although in most of the cases, affected nerves will spontaneously recover in a period, and in some cases, this undesired effect could be prolonged and persist for a few months or even make the nerve unable to fully recover.

To achieve a beneficial and effective pain control method with desired prolonged analgesic effect, there are, therefore, unmet needs for improved use of ropivacaine or other amide-type anesthetics in controlling pain. The compositions and methods of the present disclosure satisfy these and other needs.

SUMMARY

The present disclosure provides methods of treatment with specific dose ranges and dosing schedules for the amide-type anesthetic of the present disclosure that result in this prolonged effect on pain control. In particular, the present disclosure is directed to pharmacologically active agents, compositions, methods and/or dosing schedules that have certain advantages compared to the agents, compositions, methods and/or dosing schedules that are currently used and/or known in the art, including the ability to dose less frequently or to administer lower doses to obtain equivalent effects in pain control or anesthetic effects and thus reducing undesired effects of the amide-type anesthetic on the subject in need thereof. These advantages will become clear from the further description below.

The present disclosure provides a sustained-release anesthetic composition or a method of preparing the same using lyophilization (e.g., one-step lyophilization) to obtain a lipid cake comprising an amide-type anesthetic and at least one lipid, wherein a molar ratio of the amide-type anesthetic to the at least one lipid of the lipid-based complex is at least 0.5:1, and then hydrating the lipid cake with a pharmaceutically acceptable buffer solution to obtain the sustained-release anesthetic composition. This sustained-release anesthetic composition provides a rapid onset of anesthesia and a prolonged duration of local anesthesia with minimal toxicity.

In one aspect, the anesthetic composition is a pharmaceutical composition for use in treating postsurgical pain in a subject in need thereof. The pharmaceutical composition in accordance with the present disclosure comprises a lipid-based complex of an amide-type anesthetic and at least one lipid, wherein a molar ratio of the amide-type anesthetic to the at least one lipid of the lipid-based complex is at least 0.5:1, and the total amount of the amide-type anesthetic of the pharmaceutical composition is at least 1.5 to 5 times of a standard therapeutic dose of the amide-type anesthetic. The total amount of the amide-type anesthetic of the pharmaceutical composition may range from about 3 mg to about 1000 mg, from about 100 mg to about 800 mg, from about 200 mg to about 600 mg, from about 300 mg to about 600 mg, from about 300 mg to about 500 mg and optionally about 380 mg, about 475 mg, about 570 mg: or ranging from about 3 mg to about 300 mg, from about 10 mg to about 250 mg and optionally about 50 mg, about 152 mg, about 190 mg or about 228 mg. In some embodiments, the amide-type anesthetic of the pharmaceutical composition is at an amount at least about 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 to 5 times of a standard therapeutic dose of the amide-type anesthetic. Other amide-type anesthetics that may be used include lidocaine, bupivacaine, mepivacaine, levobupivacaine, the bases thereof, or combinations thereof. In some embodiments, the amide-type anesthetic is bupivacaine, ropivacaine or the base thereof.

According to the present disclosure, the lipid-based complex comprises an amide-type anesthetic and one or more lipids. In some embodiments, the lipids include at least one neutral saturated phospholipid. The at least one neutral saturated phospholipid comprises saturated fatty acids with long carbon chain with a carbon number no greater than 18.

In some embodiments, the lipid-based complex is prepared under a predetermined condition for pre-clinical use, e.g., at an ambient temperature and the saturated fatty acids with long carbon chains have a carbon number of 14, 16, and/or 18.

In some embodiments, the lipid-based complex of the anesthetic composition is formed by hydrating a lyophilized lipid cake with a pharmaceutically acceptable buffer solution at a pH higher than 5.5. The theoretically uncharged ropivacaine is 0.8% of available ropivacaine at pH 6.0 based on the calculation from its pKa (the pKa of ropivacaine is 8.1). In some embodiments, the lipid cake according to the present disclosure is prepared by dissolving apolar ropivacaine, phospholipid, and cholesterol in a solvent system, e.g., tert-butanol alone or a tert-butanol/water cosolvent, followed by removing the solvent system using a lyophilization technique.

In certain embodiments, the molar ratio of the amide-type anesthetic to the phospholipid ($mol_{drug}$:$mol_{phospholipid}$) in the lipid-based complex is at least 0.5:1. The present pharmaceutical composition can provide a sufficient amount of the amide-type anesthetic to a subject in need thereof to prolong the duration of anesthesia after in vivo local administration. In addition, a predetermined amount of the amide-type anesthetic in its free form being untrapped by the lipid-based complex can achieve rapid onset anesthesia with minimized maximum plasma concentration ($C_{max}$) exposure.

In another aspect, the present disclosure also provides methods of treating postsurgical pain in a subject in need of anesthetization. The method may comprise: administering a pharmaceutical composition of the present disclosure via a nerve block, via a field block, or via infiltration anesthesia.

In certain embodiments, the postsurgical pain is caused by surgery such as, but not limited to: hernia repair surgery, bunionectomy surgery, genitourinary surgery, orthopedic surgery, obstetrics surgery, laparoscopic surgery, abdominoplasty, breast surgery and kidney transplantation procedure (KTX).

In yet another aspect, the present disclosure provides methods of treating post-operative pain. The method may comprise: administering a dosage of the pharmaceutical composition in accordance with the present disclosure within about half an hour (30 minutes) to about three hours, optionally half an hour (30 minutes) to about two hours, and optionally half an hour to about one hour, before surgery or after the start of the surgery (during surgery) and particularly before the completion of the surgery, wherein pain reduction is at least about 2 in accordance with the Numerical Pain Rating Scale (NPRS) score for a period after surgery, wherein the period is at least 48 hours, optionally at least 72 hours, at least 96 hours or at least 168 hours. NPRS could be on a scale of 0 to 10, with 0 being no pain and 10 being the worst imaginable pain. In some embodiments, when the composition in accordance with the present disclosure is administered via a nerve block or a field block, the composition may be administered about half an hour to about one hour before surgery. In other non-limiting embodiments, when the composition in accordance with the present disclosure is administered via local infiltration, which is suitable for hernia repair surgery and bunionectomy surgery, the composition may be administered during surgery, usually at the last stages of the surgery before final closure of the incision.

Other objectives, advantages, and novel features of the disclosure will become more apparent from the following detailed description when taken in conjunction with the accompanying drawings.

DETAILED DESCRIPTION OF THE PREFERRED EMBODIMENTS

As employed above and throughout the disclosure, the following terms, unless otherwise indicated, shall be understood to have the following meanings.

As used herein, the singular forms "a", "an" and "the" include the plural reference unless the context clearly indicates otherwise.

All numbers herein may be understood as modified by "about," which, when referring to a measurable value such as an amount, a temporal duration, and the like, is meant to encompass variations of ±10%, preferably ±5%, more preferably ±1%, and even more preferably ±0.1% from the specified value, as such variations are appropriate to obtain a desired amount of amide-type anesthetic, unless other specified.

The term "treating," "treated," or "treatment," as used herein, includes preventative (e.g. prophylactic), palliative, and curative methods, uses or results. The terms "treatment" or "treatments" can also refer to compositions or medicaments. Throughout this application, by "treating" is meant a method of reducing or delaying one or more symptoms or signs of pain, the amelioration of pain as detected by art-known techniques or reduction in use of pain control medications. Art recognized methods are available to evaluate pains and its symptoms. These include, but are not limited to, 6-point descriptive pain rating scale, 11-point NPRS, visual analog scale, Wisconsin Brief Pain Questionnaire, Brief Pain Inventory, The McGill Pain Questionnaire and the short-form, McGill Pain Questionnaire and other scoring methods including Patient Global Assessment (PGA) of the method of pain control. For a human subject, self-reporting, for example using a graded scale of (0) no pain to (10) maximum pain, could be used to identify level of pain. Optionally, functional magnetic resonance imaging (fMRI) could be used in a subject to identify decreased pain following administration of a pharmaceutical composition of the present disclosure. For example, a disclosed method is considered to be a treatment if there is at least 1% reduction in one or more symptoms of pain in a subject when compared to the subject prior to treatment or one or more control subjects. Thus, the reduction can be about a 5%, 10%, 20%, 30%, 40%, 50%, 60%, 70%, 80%, 90%, 100%, or any amount of reduction in between. Treatment in a subject could also be assessed by reduction in the use of pain control medications such as opioids or other analgesics, and/or reduction in side effects associated with such analgesic medications, such as gastrointestinal symptoms related to the use of opioids. Additional efficacy questionnaires, such as the postsurgical recovery index, could be used to assess pain and recovery as well as side effects that may be associated with the use of opioids. In particular, the postsurgical pain may be acute pain and/or chronic pain. Acute pain may be experienced immediately or up to 7 days (e.g., about 1 day, 2 days, 3 days, 4 days, 5 days, 6 days or 7 days after surgery.

The term "subject" can refer to a vertebrate having or at risk of developing pain or illnesses leading to pain, or a vertebrate deemed to be in need of pain treatment or management. Subjects include all warm-blooded animals, such as mammals, including a primate, and, more preferably, a human. Non-human primates are subjects as well. The term "subject" includes domesticated animals, such as cats, dogs, etc., livestock (for example, cattle, horses, pigs, sheep, goats, etc.) and laboratory animals (for example, a mouse, rabbit, rat, gerbil, guinea pig, etc.). Thus, veterinary uses and medical formulations are contemplated herein.

"Association efficiency" (AE) represents the amount of a drug entrapped in a lipid-based complex and is calculated by the ratio of the amount of the drug in a separated lipid-based complex to the total amount of the drug in an original composition before separation. Separated lipid-based complexes can be obtained by any method known in the art. In some embodiments, separated lipid-based complexes are obtained by centrifugation methods, e.g., traditional centrifugation, density gradient centrifugation, differential centrifugation, or by filtration methods, e.g., diafiltration, gel filtration, and membrane filtration.

The term "standard therapeutic dose" can refer to an amount of indicated therapeutic agent to produce the desired effect or outcome, particularly to a compartment similar to the present disclosure, which is exemplified by an equilibration of the drug with poorly perfused tissues, such as soft tissue, muscle and fat and the like; and hard tissue, bone and the like. Standard therapeutic doses can be determined by one of ordinary skill in the art. Suitable standard therapeutic dose for each indication can refer to the references of the related anesthetics, including, but not limited to, United States Pharmacopeia (USP) and approved drug products listed in the library of Drugs@FDA sponsored by U.S. Food and Drug Administration. The therapeutic dose can be infiltrated or injected into the surgical site. For example, a standard therapeutic dose for a ropivacaine HCl solution (Naropin®) for injection for management of pain after hernia surgery by local infiltration is under 300 mg, particularly to 2 mg to 200 mg. In one embodiment, a standard therapeutic dose for a free ropivacaine solution for injection or infiltration for treatment of pain after bunionectomy surgery is 50 mg. In another embodiment, a standard therapeutic dose for Bupivacaine Hydrochloride Injection USP (by Hospira) is up to 225 mg with epinephrine 1:200,000 and 175 mg without epinephrine. Standard therapeutic doses could be determined on the basis of the type of surgery and can be established by one of ordinary skill in the art.

Amide-Type Anesthetics

The term "amide-type anesthetics" refers to one or more groups of substances causing loss of sensation in a circumscribed area of a subject caused by depression of excitation in nerve endings or inhibition of the conduction process in peripheral nerves. The typical amide-type anesthetic structure contains a lipophilic part and a hydrophilic part that connect by an —NHCO— linkage. Suitable amide-type anesthetics include, but are not limited to, lidocaine, bupivacaine, levobupivacaine, ropivacaine, mepivacaine, pyrrocaine, articaine, and prilocaine and free bases thereof. In certain embodiments, the amide-type anesthetic is ropivacaine base.

Lipid-Based Complex and Lipids

The lipid-based complex in accordance with the present disclosure comprises one or more lipids and an amide-type anesthetic. In one embodiment, the lipid-based complex may be manufactured and stored for long-term so as to extend the shelf life of the composition. The lipid-based complex may be formed by hydrating a lipid cake containing the one or more lipids and the amide-type anesthetic immediately prior to clinical use.

The lipid cake described above may comprise one or more phospholipids and the amide-type anesthetic in the absence of sterols. Alternatively, the lipid cake may comprise the amide-type anesthetic and one or more phospholipids with no more than 50% of one or more sterols, for example cholesterol, relative to the amount of the total lipids. In certain embodiments, the mole percentage of cholesterol on the basis of the total lipids is from about 0% to 50%, and optionally from about 33% to 40%. In some embodiments, the phospholipid(s) and cholesterol are at a molar ratio of from 1:1 to 3:1.

The lipid cake can be prepared by 1) dissolving one or more lipids and an amide-type anesthetics in a solvent system to form a liquid structure comprising one or more solvents to form a homogeneous solution, and 2) removing the solvent(s) to solidify the formulation of the lipids and the amide-type anesthetic(s). Solvent removal can be performed using known techniques such as freeze drying (lyophilization). Examples of solvent systems suitable for freeze drying include, but are not limited to, tert-butanol and tert-butanol/water cosolvent systems with or without other non-aqueous solvents such as acetone, acetonitrile, ethanol, n-propanol, isopropanol, n-butanol, methanol, dichloromethane, dimethyl sulfoxide, and carbon tetrachloride.

In some embodiments, the lipids of the lipid-based complex include one or more phospholipids and cholesterol, and the molar ratio of the amide-type anesthetic to the phospholipids of the lipid-based complex is at least 0.5:1, and optionally between 0.5:1 and 2:1, such as about 0.5:1, about 0.8:1, about 1:1, about 1.2:1, about 1.5:1, about 1.8:1, or about 2:1.

The one or more lipids are selected from the group consisting of dialiphatic chain lipids, such as phospholipids, diglycerides, dialiphatic glycolipids; single lipids, such as sphingomyelin and glycosphingolipid; sterols, such as cholesterol and derivates thereof; and combinations thereof. Examples of phospholipids according to the present disclosure include, but are not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoylsn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), 1-palmitoyl-2-oleoyl-sn-glycero-3-phosphoethanolamine (POPE), 1,2-distearoyl-sn-glycero-3-phosphoethanolamine (DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE).

Examples of phospholipids include, but are not limited to, dimyristoyl phosphatidylcholine (DMPC), 1,2-dilauroyl-sn-glycero-3-phosphocholine (DLPC), dipalmitoylphosphatidylcholine (DPPC), diolelphosphatidylglycerol (DOPG), 1,2-dioleoy 1-sn-glycero-3-phosphatidylcholine (DOPC), 1,2-dioleoyl-sn-glycero-3-phosphatidylserine (DOPS), diolelphosphatidic acid (DOPA), egg phosphatidylcholine (egg PC), phosphatidylethanolamine (egg PE), 1-palmitoyl-2-oleoyl-sn-glycero-3-phosphatidylethanolamine (POPE), cardiolipin, and 1,2-dimyristoyl-sn-glycero-3-phosphate (sodium salt) (DMPA).

Suitable phospholipids according to the present disclosure are saturated phospholipids derived with two saturated long carbon chain fatty acids, wherein each fatty acid has a long carbon chain of at least 12 carbons, alternatively at least 14 carbons; and no more than 20 carbons, alternatively 18 carbons, or 16 carbons. In some embodiments, the suitable saturated phospholipids according to the present disclosure are selected from the group consisting of DLPC, DMPC, DPPC, and combinations thereof.

In some embodiments, the lipid-based complex comprises liposomes and the amide-type anesthetic. The liposome comprises one or more lipids including suitable phospholipids according to the present disclosure, a positively or negatively charged phospholipid, and a determined amount of unsaturated phospholipid, wherein the determined amount is less than 10% molar percentage based on the total amount of phospholipids, for example, about 9%, 8%, 7%, 6%, 5%, 4%, 3%, 2%, or 1%.

Anesthetic Composition

The terms "anesthetic composition" and "pharmaceutical composition for use in treating pain" are interchangeably used. In certain embodiments, an anesthetic composition comprises a lipid-based complex and untrapped local anesthetic agent. In some embodiments, the lipid-based complex includes multilamellar vesicles and a local anesthetic agent entrapped in the multilamellar vesicles. The term "entrap" or "entrapment" refers to the bilayer membrane of multilamellar vesicles encapsulating, embedding, or associating with a target drug substance.

The particle size distribution of the lipid-based complex according to the present disclosure can be determined by various known methods in the art. In some embodiments, the average particle size of the lipid-based complex of the anesthetic composition is no less than 1 µm; and optionally, is more than 5 µm, such as at a range from 5 µm to 50 µm, or from 10 µm to 25 µm. Alternatively, the volume median particle diameter ($D_{50}$) of the lipid-based complex of the anesthetic composition is no less than 1 µm; and, optionally, is not less than 5 µm, such as at a range from 5 µm to 50 µm, 5 µm to 40 µm, 5 µm to 30 µm, 5 µm to 20 µm, or 5 µm to 15 µm. In some embodiments, the median particle diameter ($D_{50}$) refers to a particle diameter at which the cumulative percentage of lipid-based complex made of the agglomerated particles being 50% in the cumulative particle size distribution is 5 µm or more or 7 µm or more. In some embodiments, the median particle diameter ($D_{50}$) refers to a particle diameter at which the cumulative percentage of lipid-based complex made of the agglomerated particles being 50% in the cumulative particle size distribution is 25 µm or less, 20 µm or less, or 15 µm or less; and optionally, 5 µm to 25 µm, 5 µm to 20 µm, or 5 µm to 15 µm.

In some embodiments, a particle diameter at a cumulative percentage of 90% in a cumulative particle size distribution ($D_{90}$) of the lipid-based complex of the anesthetic composition is not less than 10 µm, such as at a range from 10 µm to 300 µm, 20 µm to 300 µm, from 20 µm to 200 µm, or from 20 µm to 100 µm. In addition, the lower limit value of $D_{90}$ is for example, but not limited to: 25 µm or more or 30 µm or more. In addition, the shape of the agglomerated particle of the lipid-based complex—for improving association efficiency per unit dosage is not particularly limited.

In some embodiments, the pharmaceutical composition for use in treating pain comprises multilamellar vesicles, a portion of the amide-type anesthetic entrapped by the multilamellar vesicles, and also a portion of the amide-type anesthetic in its free form, which is also denoted as free form amide-type anesthetic (being untrapped). The particle size distribution of the multilamellar vesicles together with the entrapped amide-type anesthetic of the lipid-based complex according to the present disclosure can be determined by various known methods in the art. In some embodiments, the particle size of the multilamellar vesicles together with the entrapped amide-type anesthetic in the anesthetic composition according to the present disclosure is no less than 1 µm; and optionally, is more than 5 µm, such as at a range from 5 µm to 200 µm, from 10 µm to 100 µm, or from 10 µm to 50 µm. Alternatively, a median diameter ($D_{50}$) of the lipid-based complex in the anesthetic composition according to the present disclosure is no less than 1 µm; and, optionally, is more than 5 µm, such as at a range from 5 µm to 100 µm, or from 10 µm to 50 µm.

In some embodiments, the lipid-based complex is formed by hydrating a lipid cake containing an amide-type anesthetic with a pharmaceutically acceptable buffer solution at a pH higher than 5.5. The anesthetic composition thus obtained may offer sustained-release of the amide-type anesthetic ready for use, or followed by dilution with the aqueous buffer solution or other adequate diluent before administration. In some embodiments, the aqueous buffer solution is at a pH range of from 5.5 to 8.0, and optionally of from 6.0 to 7.5 or from 6.5 to 7.0.

Suitable aqueous buffer solutions according to the present disclosure include, but are not limited to, citrate, acetate, malate, piperazine, succinate, 2-(N-morpholino) ethanesulfonic acid (MES), histidine, bis-tris, phosphate, ethanolamine, N-(2-acetamido)iminodiacetic acid (ADA), carbonate, N-(2-acetamido)-2-aminoethanesulfonic acid (ACES), 1,4-piperazinediethanesulfonic acid (PIPES), 3-morpholino-2-hydroxypropanesulfonic acid (MOPSO), imidazole, N,N-bis(2-hydroxyethyl)-2-aminoethanesulfonic acid (BES), 4-(2-hydroxyethyl) piperazine-1-ethanesulfonic acid (HEPES), triethanolamine, lysine, tris, and glycylglycine solutions. The amount of untrapped amide-type anesthetic in the composition can be adjusted based on the distribution-coefficient of the anesthetic by selecting an appropriate pH value for the aqueous buffer solution based on the clinical indication and the total injection dosage.

In some embodiments, the aqueous buffer solution comprises histidine at a concentration ranging from 1 mM to 200 mM, from 10 mM to 150 mM, from 20 mM to 140 mM, from 30 mM to 130 mM or from 40 mM to 120 mM.

In some embodiments, the aqueous buffer solution comprises phosphate at a concentration ranging from 1 mM to 200 mM, from 10 mM to 180 mM, 10 mM to 170 mM, from 10 mM to 160 mM, from 10 to 150 mM, 10 mM to 100 mM, from 10 mM to 75 mM, from 15 mM to 75 mM, from 15 mM to 50 mM, or from 20 mM to 50 mM.

The amount of the free form amide-type anesthetic is a function of the association efficiency (AE) of the lipid-based complex of the anesthetic composition, which is determined by a centrifugation method. Mathematically, the amount of the free form amide-type anesthetic is expressed as follows:

$$A_{untrapped} = A_{total} \times (1-AE)$$

wherein $A_{untrapped}$ is the amount of untrapped amide-type anesthetic; $A_{total}$ is the total amount of the amide-type anesthetic in the anesthetic composition; and AE is obtained by dividing the amount of the amide-type anesthetic in the lipid-based complex by the total amount of the amide-type anesthetic in the anesthetic composition. AE according to the present disclosure is at least 60%, and, optionally, from 60% to 99%, 70% to 95% and 80% to 90%.

In certain embodiments, the molar ratio of the amide-type anesthetic to the lipid(s) ($mol_{drug}:mol_{lipid}$, D:PL) of the lipid-based complex is at least 0.5:1, including but not limited to 0.7:1, 0.9:1, 1.2:1, 1.4:1 or 2:1. In certain embodiments, the median diameter ($D_{50}$) of a population of particles of the lipid-based complex is not less than 1 μm, for example, not less than 5 μm; and, optionally, within a range from 5 μm to 200 μm, from 5 μm to 190 μm, from 5 μm to 180 μm, from 5 μm to 170 μm, from 5 μm to 160 μm, from 5 μm to 150 μm, from 5 μm to 140 μm, from 5 μm to 130 μm, from 5 μm to 120 μm, from 5 μm to 110 μm, from 5 μm to 100 μm, from 10 μm to 100 μm, from 12 μm to 100 μm, from 14 μm to 100 μm, from 16 μm to 100 μm, from 18 μm to 100 μm, or from 20 μm to 100 μm.

The amide-type anesthetic concentration of the anesthetic composition may be higher than 2 mg/mL to achieve a clinical therapeutic benefit. Suitable amide-type anesthetic concentrations include but are not limited to at least 10 mg/mL, ranging from 2 mg/mL to 30 mg/mL, from 10 mg/mL to 30 mg/mL, from 10.5 mg/mL to 30 mg/mL, from 11 mg/mL to 30 mg/mL, from 11.5 mg/mL to 30 mg/mL, from 12 mg/mL to 30 mg/mL, from 12.5 mg/mL to 30 mg/mL, from 10 mg/mL to 25 mg/mL, from 10.5 mg/mL to 25 mg/mL, from 11 mg/mL to 30 mg/mL, from 11.5 mg/mL to 25 mg/mL, from 12 mg/mL to 25 mg/mL, from 12.5 mg/mL to 25 mg/mL, from 15 mg/mL to 25 mg/mL and particularly to 19 mg/mL. The restricted amount of untrapped amide-type anesthetic in the anesthetic composition of the present disclosure can provide the benefit of achieving a higher maximum tolerance dosage (depending on the plasma anesthetic concentration that causes central nervous system and cardiovascular system toxicity) and can be used to provide rapid onset of efficacy.

For clinical use, free form amide-type anesthetic in certain embodiments of the present disclosure may range from about 1% to about 50%, about 5% to about 40% or about 10% to about 30%. The remaining amide-type anesthetic in the lipid-based complex act as a depot to release the amide-type anesthetic into the local environment gradually in a manner that maintains the therapeutically effective dosage at the local site. In some embodiments, the half-life of ropivacaine, derived from a single subcutaneous administration of an anesthetic composition according to the disclosure, is prolonged at least 10-fold compared to that of unformulated ropivacaine. The duration of the anesthetic effect after administration of the anesthetic composition of the disclosure significantly extends beyond that of unformulated ropivacaine.

The pharmaceutical compositions in accordance with the present disclosure display a significant extended-release profile of the therapeutic agent and yield immediate and long-lasting pain reduction of 2 to 4 on a scale of 0 to 10 in accordance with Numerical Pain Rating Scale (NPRS) score for a period after surgery over administered a clinically relevant dose of the local anesthetic. For example, the pharmaceutical composition of the present disclosure extends the half-life of locally administered liposomal anesthetic composition. The present composition may show lower mean pain in accordance with NPRS score at all points and significantly reduced total pain after surgery at time intervals through 24 hours, 48 hours, 72 hours, 4 days, or 1 week in humans compared to that of free anesthetic or commercial anesthetic administered.

The lipid-based complex according to the present disclosure could be administered perineurally, to a surgical field or to a surgical wound. The term "postsurgical pain" and "post-operative pain" are hereby interchangeably used and refers to pain caused by various surgeries. In some embodiments, the postsurgical pain is caused by hernia repair surgery, genitourinary surgery, hemorrhoid surgery, abdominal surgery, thoracic surgery, orthopedic surgery, including, but not limited to, bunionectomy, vertebroplasty, acromioplasty, kyphoplasty, total knee or hip replacement, obstetrics surgery, breast surgery, dental surgery, abdominoplasty, breast surgery, kidney transplantation procedure (KTX) or any type of laparoscopic surgery.

The pharmaceutical composition according to the present disclosure may be injected, instilled or applied with standard syringes and needles. The injection of the pharmaceutical composition according to the present disclosure may be via subcutaneous, intradermal, or intramuscular routes.

In another embodiment, the pharmaceutical composition according to the present disclosure is administered as a nerve block as prophylactic treatment of a painful condition, such as administration prior to surgery for the treatment of postsurgical pain, in a subject in need thereof. In some embodiment, the pharmaceutical composition according to the present disclosure is administered as a nerve block such as Quadratus Lumborum Block (QLB).

A peripheral nerve block involves the introduction of an agent near or in a peripheral nerve for the reduction of pain or to provide numbness.

In another embodiment, the pharmaceutical composition according to the present disclosure is administered to a surgical field as a field block such as the Mayo block of multiple foot nerves for bunionectomy, Transversus Abdominis Plane Block (TAPB) for open laparotomy or Cesarean section, and site-specific regional anesthetic technique for total hip or knee replacement.

The disclosure will be further described with reference to the following specific, non-limiting examples.

EXAMPLES

The following examples illustrate the preparation and properties of certain embodiments of the present disclosure.

Example 1

Preparation of Anesthetic Compositions 1,2-dimyristoyl-sn-glycero-3-phosphocholine were purchased from NOF Corporation (Tokyo, Japan) or Lipoid GmbH (Ludwigshafen, Germany). Cholesterol was purchased from Sigma-Aldrich (Darmstadt, Germany) or Dishman Pharmaceuticals and Chemicals (Gujarat, India), and ropivacaine was purchased from Apollo Scientific (Cheshire, UK) or Dishman Pharmaceuticals and Chemicals. All other chemicals were purchased from Sigma-Aldrich.

To prepare the lipid cake, ropivacaine was combined with a lipid complex as indicated at a drug-to-phospholipid ratio (D:PL) of 1.458 μmol/μmol, i.e, phosphocholine:cholesterol:ropivacaine=2:1:2.9. The lipids and ropivacaine were mixed and then dissolved in tert-butanol or a tert-butanol/water cosolvent system (1/1, vol/vol) to form the liquid structure. The liquid structure was frozen and then was lyophilized overnight to obtain a lipid cake of the amide-type anesthetic.

To prepare the lipid structures for the vehicle control, phospholipids:cholesterol at a molar ratio of 2:1 was weighed and then dissolved in tert-butanol. The resulting sample was frozen and then was lyophilized overnight to obtain a lipid cake of the vehicle control.

The lipid cakes of the anesthetic or the vehicle control were hydrated with a buffer solution at pH 6.5 to 6.8 at a temperature no lower than ambient temperature (AT) (25° C.) to form an anesthetic composition and a vehicle control composition respectively, followed by characterization of association efficiency and particle size distribution.

Characterization of Anesthetic Compositions

The association efficiency (AE) of each of the preparations as described above was determined as follows. An aliquot of two hundred microliters of each sample of the anesthetic composition was centrifuged for 5 min at 3000×g at 4° C. to obtain a lipid-based complex. After decanting the supernatant, the lipid-based complex was re-suspended to a final volume of 200 μL. A reference absorbance standard was established for each drug substance (e.g., ropivacaine) based on solutions of the test drug substance of known concentration. The drug amounts of both the original anesthetic composition and the lipid-based complex were measured using an ultraviolet/visible (UV/Vis) spectrophotometer. The AE represents the ratio of the drug amount in the lipid-based complex to the amount of the drug substance in the original anesthetic composition. The D:PL of the lipid-based complex was calculated by multiplying the D:PL of the lyophilized lipid cake by AE and denoted as "resultant D:PL."

The particle size of each anesthetic composition was measured using a laser diffraction analyzer (LA-950V2, Horiba). The median diameter ($D_{50}$) of the lipid-based complex formed by hydrating the lyophilized lipid cake with a pharmaceutically acceptable buffer solution (e.g., 50 mM histidine buffer at pH 6.5) was examined.

The lipid-based complex in the anesthetic composition was determined to have a resultant drug to phospholipid ratio of about 1.32. The median diameter ($D_{50}$) of population of particles of the lipid-based mixture in the anesthetic composition was about 5 μm to 10 μm.

Example 2 Treatment of Pain in Adult Subjects Following Inguinal Hernia Repair Surgery A Phase I/II, randomized, double-blind, comparator-controlled, dose-escalation study to assess the safety, PK, and efficacy of single postsurgical application of the anesthetic composition in accordance with the present disclosure (denoted as TLC590) compared with Naropin® via a single infiltrative local administration in adult subjects following inguinal hernia repair surgery.

The study enrolled approximately 64 evaluable subjects who met all entry criteria across 4 cohorts. Dose escalation of a single postsurgical administration of TLC590 was performed using sequential dose levels, as compared with Naropin®. Dose-escalation were determined by review of treatment-related adverse events (TEAEs) and all serious AEs (SAEs) by a safety monitoring committee (SMC).

Inclusion Criteria were listed as below:
1. able and willing to provide a written informed consent;
2. male or female between 18 and 65 years of age, inclusive;
3. scheduled to undergo a primary, unilateral Lichtenstein inguinal hernia repair with mesh, and be able to use the anesthesia regimen;
4. have an ASA Physical Status Classification of 1 or 2;
5. female subjects are eligible only if: not pregnant; not lactating; not planning to become pregnant during the study; commits to the use of an acceptable form of birth control; or male subjects must be sterile or commit to the use of a reliable method of birth control for the duration of the study until at least 1 week after the administration of blinded study medication; and
6. have a body mass index ≤35 kg/m².

Figure 1:
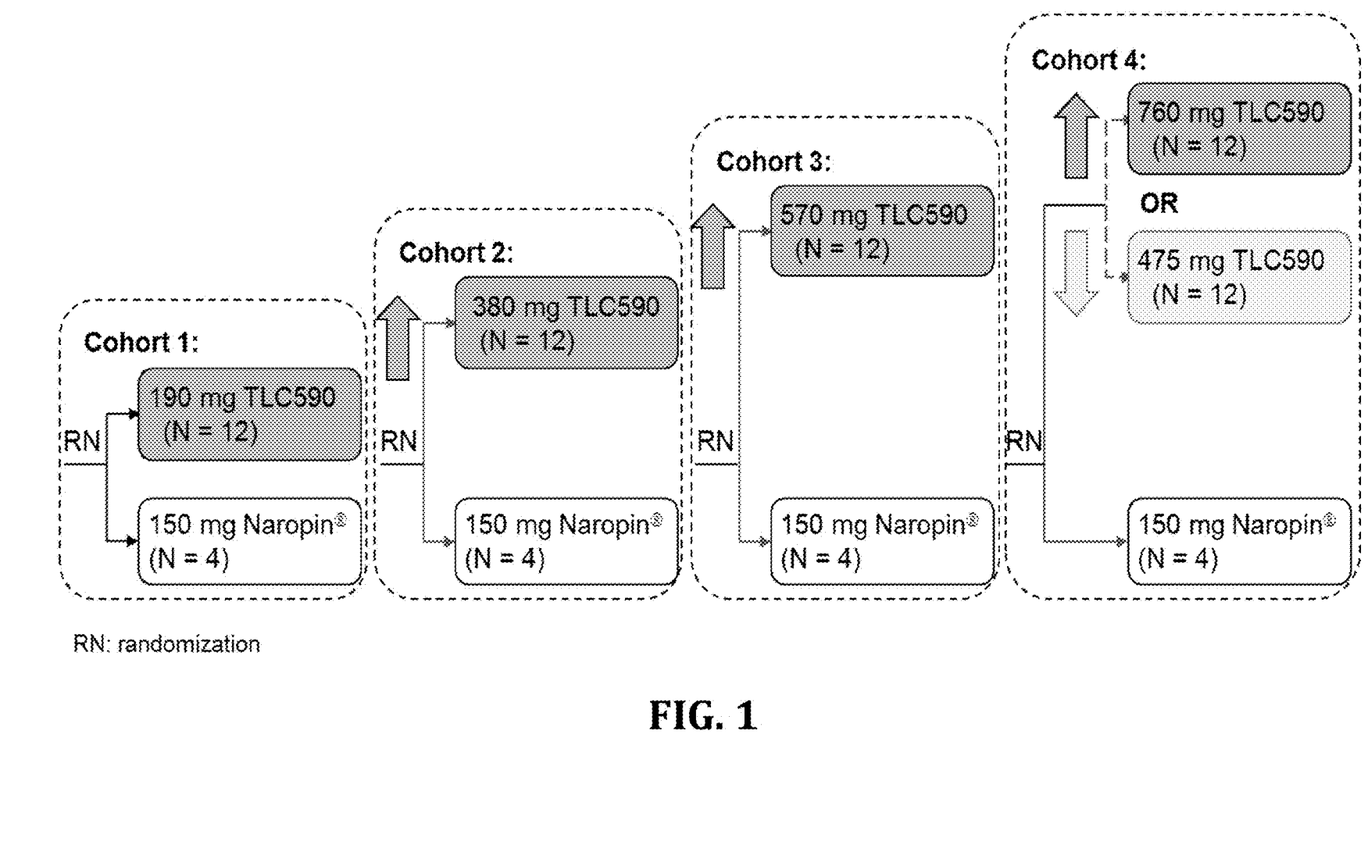
FIG. 1 illustrates the study design for a clinical trial of the anesthetic composition of the present disclosure for the treatment of postsurgical pain after hernia repair surgery.

Subjects were enrolled to each cohort in a 3:1 ratio. Each cohort comprised subjects receiving a dose of TLC590 or active comparator drug (Naropin® 150 mg; [0.5%, 5 mg/mL]) in accordance with the randomization schedule and dose-escalation scheme (FIG. 1).

To maintain objectiveness, the study drug was managed and administered by an independent unblinded team, including injectors, pharmacists, and clinical research associates. Subjects, investigators, and all other site staff who directly interact with subjects, evaluate safety and efficacy, and collect subject data, remained blinded and must not communicate or discuss any study information with the unblinded team.

The arms and interventions were designed as below:

Arms

Experimental: TLC590 group:

TLC590 (Ropivacaine composition) is a sustained-release liposome formulation of ropivacaine, white aqueous suspension with ropivacaine concentration at approximately 19 mg/mL.

Active Comparator: Naropin®:

Naropin® injection contains ropivacaine HCl. Strength: 150 mg/30 mL (5 mg/mL)

Size: 30 mL fill, in a 30 mL single dose vial.

Interventions

Drug: TLC590 (Ropivacaine composition).

TLC590 lipid cake was reconstituted with the TLC590 reconstitution solution to form the TLC590 anesthetic composition.
Drug: Naropin®
Local infiltration of Naropin® to produce anesthesia for surgery and analgesia in post-operative pain management. Naropin® 150 mg [0.5%, 5 mg/mL]×30 mL Other Name: Naropin®, 0.5% Injectable Solution.
Primary Outcome Measures were listed below: Safety and tolerability: (i) number of SAEs and treatment-related severe AEs (to determine MTD) [Time Frame: Screening till 30 days post IP administration] and;
Secondary Outcome Measures were listed below:
1. Pain intensity at rest and with movement assessed using an 11-point NPRS ranging from a score of 0 (no pain) to 10 (worst possible pain).
2. Patient Global Assessment (PGA) of the method of pain control (poor, fair, good, or excellent).
3. AUC of NPRS at rest and with movement.
4. Cumulative proportion of pain-free (defined as an NPRS at rest of 0 or 1) subjects at scheduled timepoints.
5. Proportion of pain-free (defined as an NPRS at rest of 0 or 1) subjects at scheduled timepoints.
6. Cumulative proportion of subjects who used no rescue analgesic through 12, 24, 36, 48, 72, and 96 hours.
7. Time to the first post-operative use of rescue analgesics.
8. Total post-operative consumption of each type of rescue analgesics through 12, 24, 36, 48, 72, and 96 hours.
9. Average daily rescue analgesic consumption by type through 24, 48, 72 and 96 hours.
10. Integrated analgesic score using NPRS score and rescue analgesic consumption.
11. Cumulative proportion of subjects who used no postoperative antiemetic therapy through 12, 24, 36, 48, 72, and 96 hours.
12. Incidence of all adverse events by severity and relatedness.
13. Exposure-response relationship between PK parameters and NPRS scores.

Changes from the screen above were analyzed with statistics. Therapy of TLC590 via a single infiltrative local administration at a dose of 190 mg, 380 mg, 475 mg and 570 mg resulted in a beneficial clinical response according to any one or more of the endpoints noted above.

Results

Figure 1A:
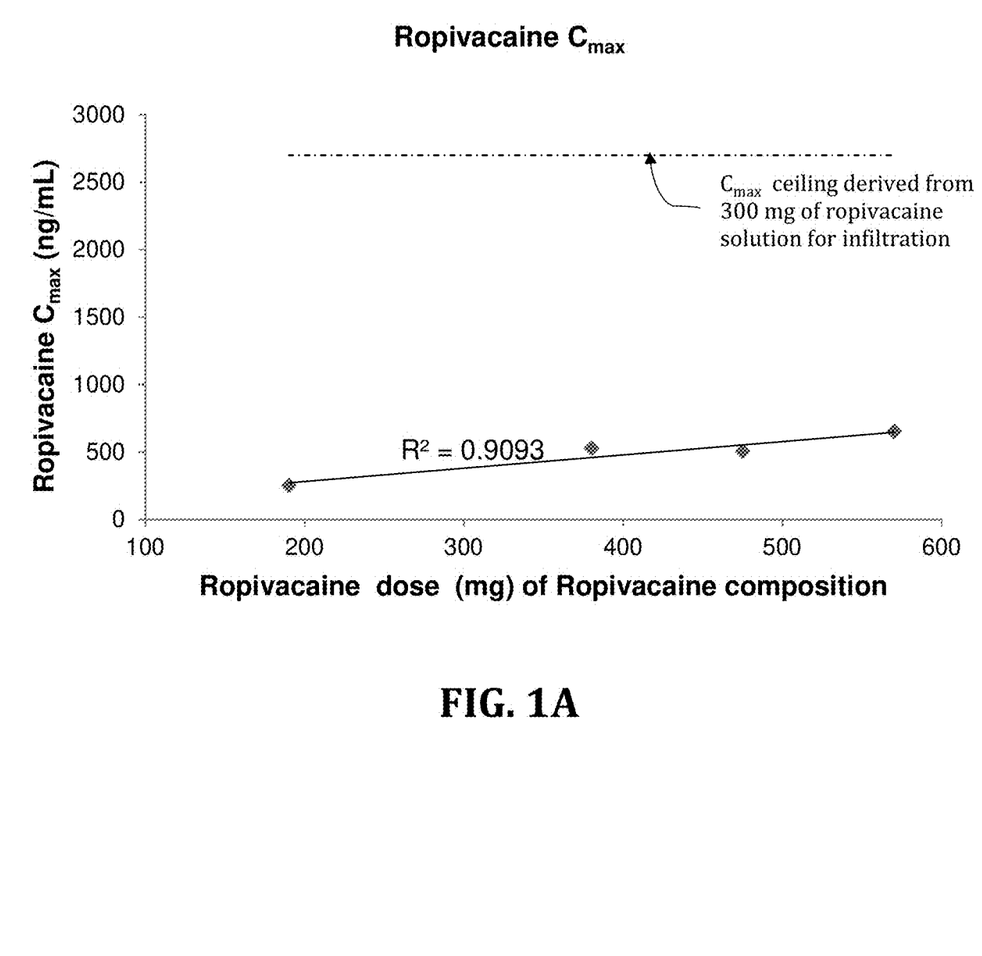
FIG. 1A illustrates a chart comparing the maximal plasma concentration of ropivacaine after treatment of postsurgical pain with the anesthetic composition of the present disclosure with various administered amounts as indicated.
Figure 2:
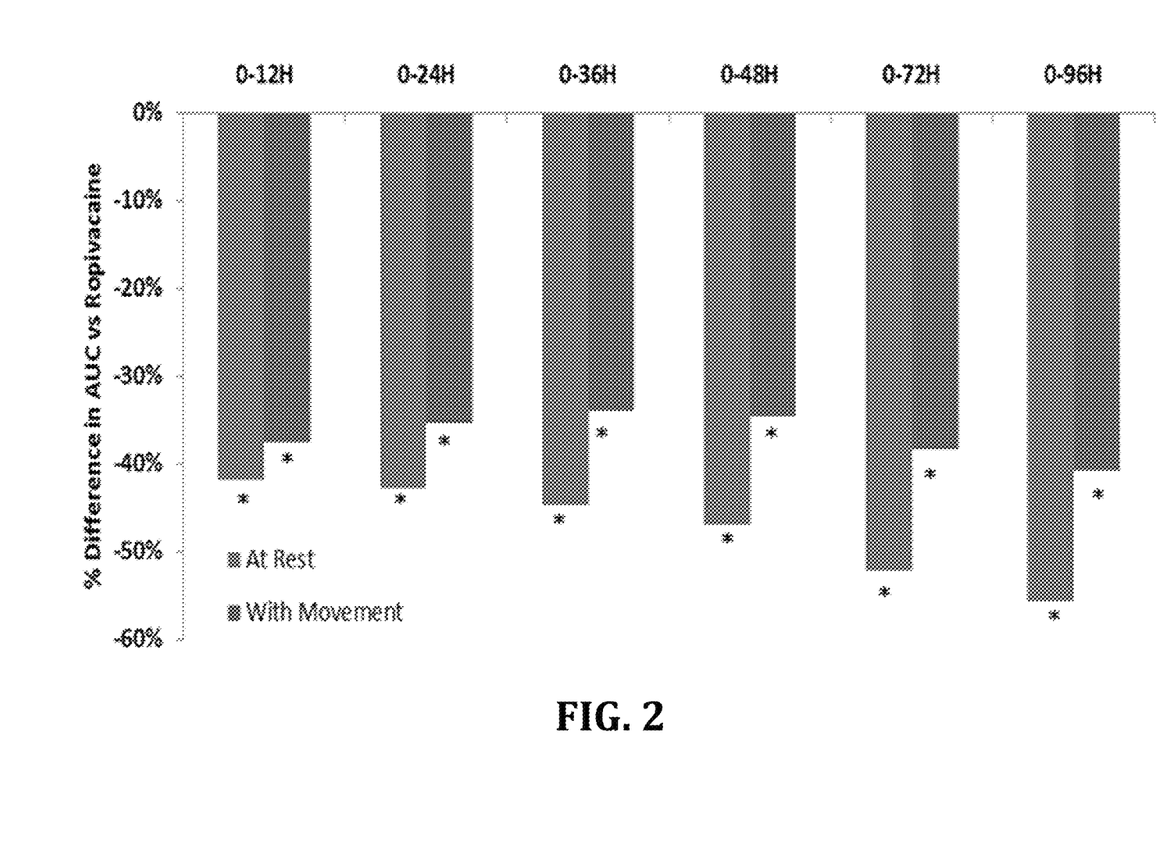
FIG. 2 illustrates the study results for a clinical trial of the anesthetic composition of the present disclosure, wherein AUC=area under the pain-time curve: LS=least squares: NPRS=numerical pain rating scale: LS means from an ANOVA model including NPRS AUC as the response and treatment group as fixed main effect: NPRS adjusted for use of rescue medication using windowed worst observation carried forward (wWOCF): *$p<0.05$ vs Ropivacaine.
Figure 3:
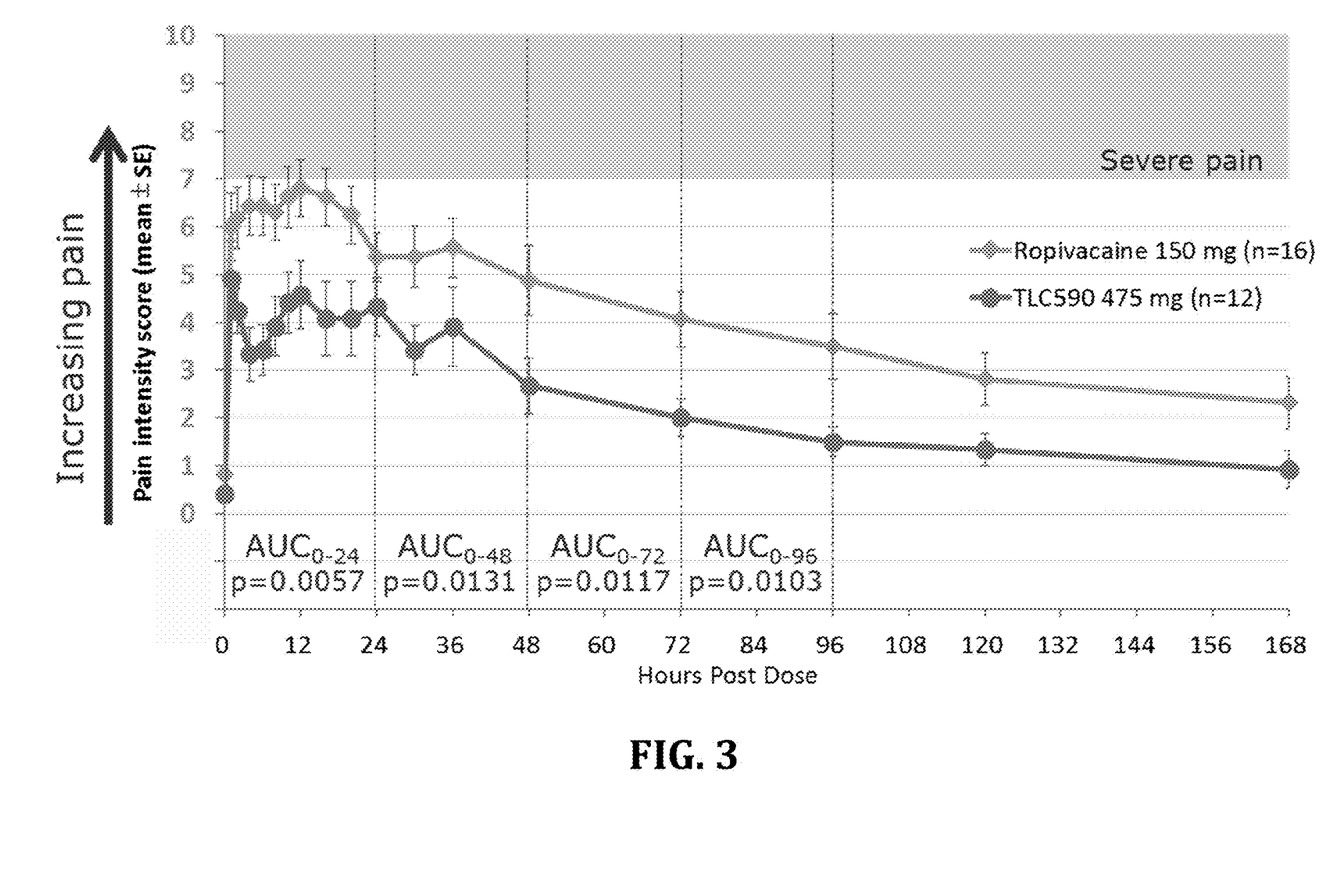
FIG. 3 illustrates LS Mean (SE) Pain with Movement for the anesthetic composition of the present disclosure at a dose of 475 mg compared to ropivacaine, wherein LOCF (last observation carried forward) is for missing data; and wWOCF (windowed-worst observation carried forward) is for rescue medication.

A total of 64 subjects were randomized into four cohorts. No serious adverse events or events of local anesthetic systemic toxicity (LAST) were observed in the study. All 4 TLC590 dose groups showed similar safety and tolerability as ropivacaine 150 mg. Even at 570 mg, the mean maximum plasma unbound ropivacaine concentration of TLC590 was lower than that of the ropivacaine group. Mean plasma concentrations for TLC590 doses remained at plateau for around 24 hours and declined with observed $t_{1/2}$ significantly longer than the ropivacaine group and $C_{max}$ lower than one-fifth of that of 300 mg of 7.5 mg/mL ropivacaine solution for infiltration (2.7 mg/mL) (Regional Anesthesia and Pain Medicine 23 (2): 189-196, 1998) (FIG. 1A). All 4 doses of TLC590 had reduced postsurgical pain relative to the ropivacaine group, as measured by least squares (LS) mean area under the pain curves (AUC) for NPRS. For TLC590 475 mg there were durable, statistically significant and clinically meaningful reductions in pain intensity with movement and at rest over time (FIG. 2) compared to ropivacaine (all p<0.05; highest p-value of 0.0131); reduced pain vs. ropivacaine was maintained through 168 hours (FIG. 3). Median time to first rescue analgesic was 3.2 times as long for TLC590 475 mg than ropivacaine group (42 hours vs 13 hours). The majority (58.3%) of TLC590 (475 mg)-treated patients did not use any rescue opioids throughout the study. Among those who did use rescue opioid, the median time to first postsurgical opioid use was about 4 times that of the ropivacaine group (13.0 hours vs 3.3 hours). Mean total opioid consumption was 54% less than that of the ropivacaine group through 96 hours post surgery.

Conclusion

TLC590 showed similar safety and tolerability as ropivacaine with no LAST events, and yielded immediate and long-lasting pain reduction over those with ropivacaine, reducing or eliminating the need for opioids. Subjects receiving TLC590 475 mg showed superiority to a clinically relevant dose of the approved drug, ropivacaine, with lower mean pain at all points and significantly reduced total pain at time intervals through 4 days after surgery.

Example 3 Treatment of Pain in Adult Subjects Following Bunionectomy Surgery

A Phase II, randomized, double-blind, comparator- and placebo-controlled study had been conducted to assess the safety, PK, and efficacy of single postsurgical application of TLC590 compared with Naropin® or bupivacaine and placebo via a single infiltrative local administration in adult subjects following bunionectomy surgery.

Approximately 223 eligible subjects were enrolled in this study. The study was divided into two parts:

Part 1: Blinded Pharmacokinetics of TLC590 and Naropin®, approximately 48 subjects were randomized at a ratio of 1:1:1:1 to treatment with TLC590 152 mg (8 mL), TLC590 190 mg (10 mL), TLC590 228 mg (12 mL), or Naropin® (50 mg; 10 mL). Randomization schedule was assigned by a centralized interactive web response system (IWRS). An unblinded interim analysis was performed to review the safety, efficacy, and pharmacokinetics of the 3 doses of TLC590 and Naropin® in Part 1 of the trial.

Figure 4:
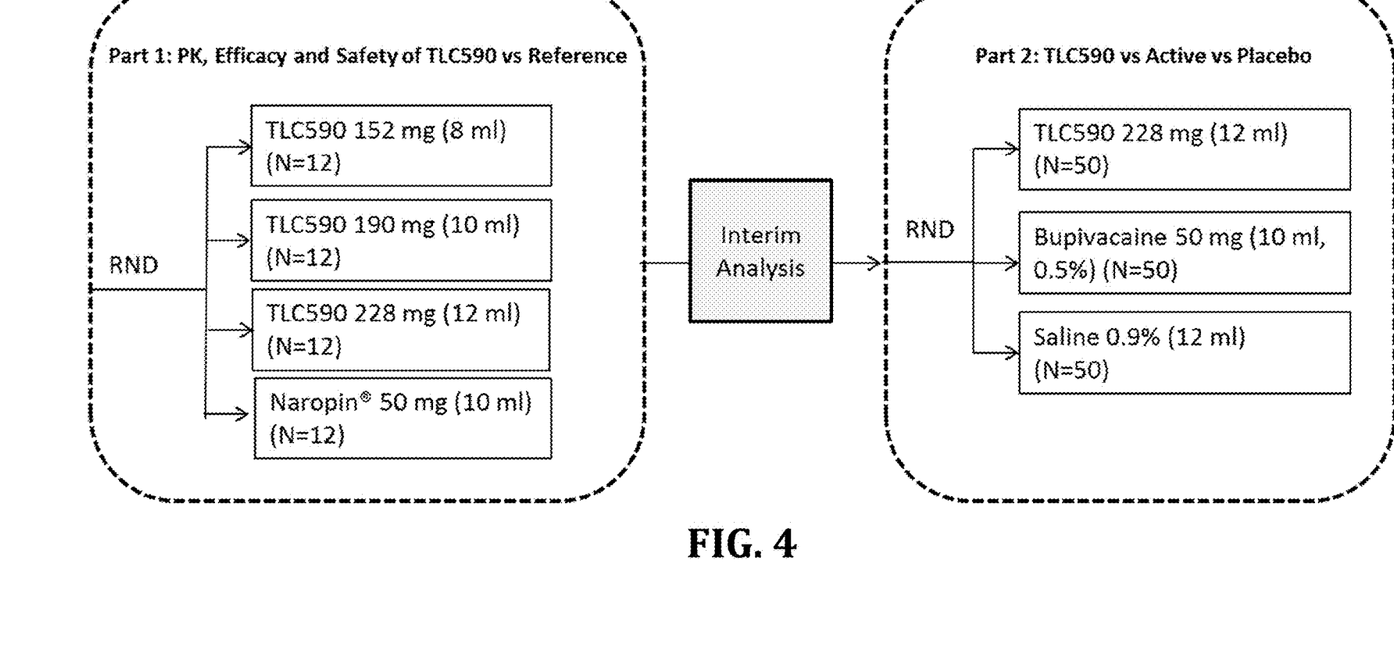
FIG. 4 illustrates the study design for a clinical trial of the anesthetic composition of the present disclosure for the treatment of postsurgical pain after bunionectomy surgery.

Part 2: Efficacy and Safety of TLC590 versus bupivacaine and placebo, Part 2 of the study enrolled approximately 150 subjects who meet all entry criteria with ratio of 1:1:1 randomization to the treatment of TLC590 228 mg, bupivacaine, and placebo. Randomization schedule was assigned by a centralized IWRS. Study design scheme is shown in FIG. 4.

Changes from the screen above were analyzed with statistics. Therapy of TLC590 via a single infiltrative local administration at a dose of 152 mg, 190 mg and 228 mg resulted in a beneficial clinical response according to any one or more of the endpoints noted above.

What is claimed is:

1. A pharmaceutical composition for treating postsurgical pain, which comprises a lipid-based complex at a pH of 5.5 to 8.0, wherein the lipid-based complex comprises an amide-type anesthetic in a free base form and a neutral saturated phospholipid, wherein a molar ratio of the amide-type anesthetic in a free base form to the neutral saturated phospholipid of the lipid-based complex is between 0.5:1 and 2:1, and wherein the total amount of the amide-type anesthetic in a free base form of the pharmaceutical composition ranges from 10 mg to 800 mg per dose.

2. The pharmaceutical composition of claim 1, wherein the total amount of the amide-type anesthetic in a free base form ranges from 300 mg to 600 mg per dose.

3. The pharmaceutical composition of claim 2, wherein the total amount of the amide-type anesthetic in a free base form is 475 mg per dose.

4. The pharmaceutical composition of claim 2, wherein the postsurgical pain is caused by hernia repair surgery.

5. The pharmaceutical composition of claim 1, wherein the total amount of the amide-type anesthetic in a free base form ranges from 10 mg to 300 mg per dose.

6. The pharmaceutical composition of claim 5, wherein the total amount of the amide-type anesthetic in a free base form is 190 mg per dose.

7. The pharmaceutical composition of claim 5, wherein the postsurgical pain is caused by bunionectomy surgery.

8. The pharmaceutical composition of claim 1, wherein the pharmaceutical composition comprises 10 mg/mL to 30 mg/mL of the amide-type anesthetic in a free base form.

9. The pharmaceutical composition of claim 1, wherein the pharmaceutical composition comprises 15 mg/mL to 25 mg/mL of the amide-type anesthetic in a free base form.

10. The pharmaceutical composition of claim 1, wherein the neutral saturated phospholipid comprises one or more saturated fatty acids, each saturated fatty acid independently comprising a carbon chain of carbon number no greater than 18.

11. The pharmaceutical composition of claim 1, wherein the neutral saturated phospholipid is selected from the group consisting of dimyristoyl phosphatidylcholine (DMPC), 1,2-dilauroyl-sn-glycero-3-phosphocholine (DLPC), dipalmitoylphosphatidylcholine (DPPC) and combinations thereof.

12. The pharmaceutical composition of claim 1, wherein the lipid-based complex further comprises a sterol.

13. The pharmaceutical composition of claim 12, wherein the sterol is cholesterol.

14. The pharmaceutical composition of claim 1, wherein the amide-type anesthetic is selected from the group consisting of lidocaine, bupivacaine, levobupivacaine, ropivacaine, mepivacaine, pyrrocaine, articaine, prilocaine, and combinations thereof.

15. The pharmaceutical composition of claim 1, wherein a median diameter of the lipid-based complex ranges from 5 μm to 200 μm.

16. The pharmaceutical composition of claim 1, wherein the amide-type anesthetic is ropivacaine.

17. The pharmaceutical composition of claim 5, wherein the total amount of the amide-type anesthetic in a free base form is 152 mg per dose.

18. The pharmaceutical composition of claim 5, wherein the total amount of the amide-type anesthetic in a free base form is 228 mg.

* * * * *